United States Patent
Karolchyk et al.

(10) Patent No.: US 11,185,546 B2
(45) Date of Patent: Nov. 30, 2021

(54) PHARMACEUTICAL FORMULATIONS FOR THE TREATMENT OF DRY EYE AND METHODS FOR FABRICATING AND USING THEREOF

(71) Applicant: Harrow IP, LLC, Nashville, TN (US)

(72) Inventors: John Scott Karolchyk, Lake Hopatcong, NJ (US); John P. Saharek, Nashville, TN (US)

(73) Assignee: Harrow IP, LLC, Nashville, TN (US)

( * ) Notice: Subject to any disclaimer, the term of this patent is extended or adjusted under 35 U.S.C. 154(b) by 0 days.

(21) Appl. No.: 16/871,692

(22) Filed: May 11, 2020

(65) Prior Publication Data

US 2020/0268763 A1 Aug. 27, 2020

Related U.S. Application Data

(62) Division of application No. 16/523,059, filed on Jul. 26, 2019, now Pat. No. 10,695,351.

(60) Provisional application No. 62/711,862, filed on Jul. 30, 2018.

(51) Int. Cl.
| | | |
|---|---|---|
| *A61K 31/522* | (2006.01) | |
| *A61K 9/00* | (2006.01) | |
| *A61K 31/7072* | (2006.01) | |
| *A61K 31/7076* | (2006.01) | |
| *A61K 31/497* | (2006.01) | |
| *A61K 47/34* | (2017.01) | |
| *A61K 38/13* | (2006.01) | |
| *A61K 31/436* | (2006.01) | |
| *A61K 47/38* | (2006.01) | |
| *A61K 47/32* | (2006.01) | |
| *A61K 31/4196* | (2006.01) | |

(52) U.S. Cl.
CPC .......... *A61K 31/522* (2013.01); *A61K 9/0048* (2013.01); *A61K 31/4196* (2013.01); *A61K 31/436* (2013.01); *A61K 31/497* (2013.01); *A61K 31/7072* (2013.01); *A61K 31/7076* (2013.01); *A61K 38/13* (2013.01); *A61K 47/32* (2013.01); *A61K 47/34* (2013.01); *A61K 47/38* (2013.01)

(58) Field of Classification Search
CPC .............. A61K 9/0048; A61K 31/4196; A61K 31/436; A61K 31/497; A61K 31/7072; A61K 31/7076; A61K 38/13; A61K 47/32; A61K 47/34; A61K 47/38
See application file for complete search history.

(56) References Cited

U.S. PATENT DOCUMENTS

| | | | |
|---|---|---|---|
| 4,911,926 A * | 3/1990 | Henry | A61P 1/00 424/78.06 |
| 6,034,088 A * | 3/2000 | Reeve | A61L 31/041 514/263.31 |
| 6,204,270 B1 | 3/2001 | Ron et al. | |
| 9,849,133 B2 | 12/2017 | Buderer | |
| 10,383,875 B2 | 8/2019 | Buderer et al. | |
| 10,561,607 B2 * | 2/2020 | Karolchyk | A61K 31/7036 |
| 10,695,351 B2 * | 6/2020 | Karolchyk | A61K 31/4196 |
| 2003/0050318 A1 * | 3/2003 | Shirley | A61Q 19/06 514/263.35 |
| 2003/0077328 A1 * | 4/2003 | Reeve | C08L 71/02 424/486 |
| 2009/0098136 A1 | 4/2009 | Gamache et al. | |
| 2010/0183519 A1 * | 7/2010 | Katz | A61P 17/02 424/9.2 |
| 2011/0104206 A1 | 5/2011 | Nanduri et al. | |
| 2015/0017151 A1 | 1/2015 | Buderer | |
| 2015/0335704 A1 | 11/2015 | Karolchyk | |
| 2016/0193213 A1 * | 7/2016 | Baum | A61K 31/522 424/94.67 |
| 2017/0112936 A1 | 4/2017 | Karolchyk et al. | |
| 2017/0319590 A1 | 11/2017 | Buderer et al. | |
| 2020/0030334 A1 | 1/2020 | Karolchyk et al. | |
| 2020/0155450 A1 * | 5/2020 | Karolchyk | A61K 31/7036 |

FOREIGN PATENT DOCUMENTS

JP  2003-201241 A  7/2003

OTHER PUBLICATIONS

Dorner et al. "Effects of Pentoxifylline and Alprostadil on Ocular Hemodynamics in Healthy Humans," IOVS, Feb. 2007, 48(2):815-819.

Kruger et al. "Short-term Oral Pentoxifylline Use Increases Choroidal Blood Flow in Patients With Age-related Macular Degeneration," Arch Ophthalmol, Jan. 1998, 116:27-30.

Schmetterer et al. "A Randomized, Placebo-controlled, Double-blind Crossover Study of the Effect of Pentoxifylline on Ocular Fundus Pulsations," American Journal of Ophthalmology, 1996,121(2):169-176.

* cited by examiner

*Primary Examiner* — Daniel R Carcanague

(57) ABSTRACT

Methods and kits for improving tear production are described, along with topical pharmaceutical compositions. In certain instances, the composition comprises pentoxifylline and a pharmaceutically acceptable carrier. The compositions also may further comprise another active agent, such as an anti-bacterial agent, antiviral agent, antifungal agent, or immunosuppressant agent, and combinations thereof.

13 Claims, No Drawings

PHARMACEUTICAL FORMULATIONS FOR THE TREATMENT OF DRY EYE AND METHODS FOR FABRICATING AND USING THEREOF

CROSS REFERENCE TO RELATED APPLICATION(S)

This application is a divisional of U.S. Ser. No. 16/523,059, filed Jul. 26, 2019, currently pending, which claims the benefit of priority under 35 U.S.C. § 119(e) of U.S. Ser. No. 62/711,862, filed Jul. 30, 2018, the entire content of each of which is incorporated herein by reference.

FIELD OF THE INVENTION

The present invention relates generally to the field of ophthalmology and more specifically to compositions and methods designed to treat, mitigate or prevent dry eye syndrome in mammals, and to methods of preparing such compositions.

BACKGROUND

Dry eye is an ocular disease that results in symptoms of discomfort and visual disturbance as a result of decreased tear production, and is characterized by a dysfunction of one or more components of the tear film, the latter being stable in the absence of this disease. Tear deficiency may be caused by poor production of tears as a result of age, hormonal changes, various autoimmune diseases and other factors, and may be also a side effect of certain medications, such as beta-blockers, antidepressants, antihistamines etc. However, normal stable condition of the tear film resulting in normal tear secretion is important for the lubrication and maintenance of the refractive surface of the eye.

Dry eye may afflict an individual with varying degrees of severity, ranging from burning sensation, a feeling of dryness and persistent irritation up to substantial impairment of vision in more severe cases, vision may be substantially impaired. Therefore, a variety of approaches have been developed for treatment and therapy. Typically the majority of patients with dry eye syndrome are prescribed or recommended artificial tears. Other methods and devices that are also often recommended include scrubs, drops, inserts, plugs or lid compresses. These products typically comprise immunologic agents, autologous compounded serum, mucin producing agents or lubricants. While some such remedies do exist and may provide some relief in some cases, in many other instances they are insufficient or too expensive. Accordingly, it is desirable to have better alternative compositions.

This patent specification discloses such pharmaceutical compositions suitable for treatment and alleviation of dry eye disease that can achieve positive patient outcomes while free of drawbacks and deficiencies of existing formulations, and methods of fabricating and administering the same.

SUMMARY

According to one embodiment of the invention, a method for improving tear production in a mammalian subject suffering from insufficient secretion thereof is provided. The method includes administering to the subject a pharmaceutical formulation comprising a therapeutically effective amount of a compound of formula I:

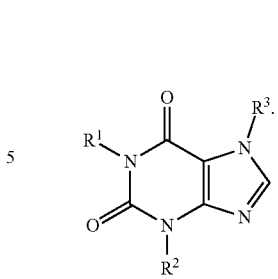

or a pharmaceutically acceptable salt, solvate or hydrate thereof, wherein each of $R^1$, $R^2$ and $R^3$ is H, a $C_1$-$C_6$ alkyl, a $C_2$-$C_6$ alkenyl, a $C_2$-$C_6$ alkynyl, a cycloalkyl, a heterocyclyl, an aryl and a heteroaryl, each of which is further optionally substituted.

According to another embodiment of the invention, the compound of formula I shown above is pentoxifylline.

According to yet another embodiment of the invention, the methods disclosed herein are useful for treating the insufficient tear secretion that is caused by a disease, syndrome or pathology such as keratoconjunctivitis sicca, Stevens-Johnson syndrome, age-related dry eye, ocular cicatricial pemphigoid, neurotrophic ocular surface disease and/or blepharitis.

According to other embodiments of the invention, the pharmaceutical compositions described herein may be delivered topically, e.g., can be formulated and delivered to a patient as eye drops.

DETAILED DESCRIPTION

A. Terms and Definitions

Unless specific definitions are provided, the nomenclatures utilized in connection with, and the laboratory procedures and techniques of analytical chemistry, synthetic organic and inorganic chemistry described herein, are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, formulating compositions and testing them. The foregoing techniques and procedures can be generally performed according to conventional methods well known in the art.

It is to be understood that both the foregoing general description and the following detailed description are exemplary and explanatory only and are not restrictive of the invention claimed. As used herein, the use of the singular includes the plural unless specifically stated otherwise. The section headings used herein are for organizational purposes only and are not to be construed as limiting the subject matter described.

As used herein, "or" means "and/or" unless stated otherwise. Furthermore, use of the term "including" as well as other forms, such as "includes," and "included," is not limiting.

"About" as used herein means that a number referred to as "about" comprises the recited number plus or minus 1-10% of that recited number. For example, "about" 100 degrees can mean 95-105 degrees or as few as 99-101 degrees depending on the context. Whenever it appears herein, a numerical range such as "1 to 20" refers to each integer in the given range; i.e., meaning only 1, only 2, only 3, etc., up to and including only 20.

The term "pharmaceutical composition" is defined as a chemical or biological compound or substance, or a mixture or combination of two or more such compounds or substances, intended for use in the medical diagnosis, cure, treatment, or prevention of disease or pathology.

The term "dry eye" or "dry eye syndrome" is defined as one or several conditions associated with, or caused by, either decreased tear production or increased tear film evaporation, or both, and characterized by redness, itching, and burning of the eye. Dry eye syndrome is inclusive of keratoconjunctivitis sicca.

The terms "anti-bacterial" and "antibiotic" used herein interchangeably, refer to any substance or compound that destroy bacteria and/or inhibit the growth thereof via any mechanism or route.

The term "anti-viral" refers to any substance or compound that counteract or suppress any viral substance via any mechanism or route.

The term "immunosuppressant" refers to any substance or compound that can suppress, reduce or prevent the immune response.

The term "tumor necrosis factor" refers to any protein that is capable of inducing death of tumor cells; accordingly, a tumor necrosis factor "antagonist" or "inhibitor" refers to any compound or substance that is capable of counteracting of a tumor necrosis factor or suppressing, diminishing or reducing body's response to it.

The term "salt" refers to an ionic compound which is a product of the neutralization reaction of an acid and a base.

The terms "solvate" and "hydrate" are used herein to indicate that a compound or substance is physically or chemically associated with a solvent for "solvates" such as water (for "hydrates").

The term "carrier" refers to a substance that serves as a vehicle for improving the efficiency of delivery and the effectiveness of a pharmaceutical composition.

The term "excipient" refers to a pharmacologically inactive substance that is formulated in combination with the pharmacologically active ingredient of pharmaceutical composition and is inclusive of bulking agents, fillers, diluents and products used for facilitating drug absorption or solubility or for other pharmacokinetic considerations.

The term "therapeutically effective amount" is defined as the amount of the compound or pharmaceutical composition that will elicit the biological or medical response of a tissue, system, animal or human that is being sought by the researcher, medical doctor or other clinician.

The term "pharmaceutically acceptable" when used to describe a carrier, whether diluent or excipient, refers to a substance that is compatible with the other ingredients of the formulation and not deleterious to the recipient thereof.

The terms "administration of a composition" or "administering a composition" is defined to include an act of providing a compound of the invention or pharmaceutical composition to the subject in need of treatment.

B. Embodiments of the Invention

According to embodiments of the present invention, methods for improving tear production in a mammalian subject suffering from insufficient secretion thereof are provided. The methods include administering to the subject a pharmaceutical formulation comprising a therapeutically effective amount of a tumor necrosis factor antagonist or inhibitor (TNF) such as a compound of formula I:

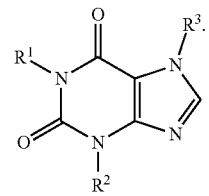

I or a pharmaceutically acceptable salt, solvate or hydrate thereof, wherein each of $R^1$, $R^2$ and $R^3$ is H, a $C_1$-$C_6$ alkyl, a $C_2$-$C_6$ alkenyl, a $C_2$-$C_6$ alkynyl, a cycloalkyl, a heterocyclyl, an aryl and a heteroaryl, each of which is further optionally substituted. The composition may include a single compound of formula I or a combination of several such compounds each of which is described by formula I. The quantity of compound of formula I in the pharmaceutical formulation expressed as molar concentration can be between about 0.03 mM and about 3 mM of compound of formula I per 1 µL of the entire formulation.

In one embodiment the compound of formula I is pentoxifylline, i.e., 1-(5-oxohexyl)-3,7-dimethylxanthine, a compound of formula I where each of $R^2$ and $R^3$ is methyl and $R^1$ is 5-oxohehyl, i.e., a functional group having the structure —$(CH_2)_4$—$C(O)$—$CH_3$. Lisofylline, an active metabolite of pentoxifylline, i.e., 1-(5-hydroxyhexyl)-3,7-dimethyl-3,7-dimethylxanthine can be also used if desired. The structure of lisofylline is basically the same as that of pentoxifylline except its functional group $R^1$ includes a primary alcohol moiety —C(OH)— instead of the acyl moiety —C(O)— that is present in the $R^1$ group in pentoxifylline. Other non-limiting examples of compounds encompassed by formula I that can be used include aminophylline, enprofylline and isbufylline.

The pharmaceutical formulations that are described herein may in addition optionally contain other pharmacologically active compounds such as at least one anti-bacterial agent(s), at least one antiviral medicament(s), at least one antifungal medicament(s), at least one immunosuppressant(s) and combinations thereof. Those having ordinary skill in the art can determine what specific anti-bacterial, antiviral, antifungal medicament(s) and/or immunosuppressant(s) are to be used, if any.

In various embodiments, the concentration of the anti-bacterial agent(s) in the ophthalmological compositions of the present application may be between about 0.01 mg/mL and about 50.0 mg/mL, such as between about 0.5 mg/mL and about 10.0 mg/mL, for example, about 1.0 mg/mL. Non-limiting examples of the anti-bacterial agents that may be used include fluoroquinolones such as moxifloxacin, gatifloxacin, nalidixic acid, oxolinic acid, piromidic acid, pipemidic acid, rosoxacin, enoxacin, fleroxacin, lomefloxacin, nadifloxacin, ofloxacin, pefloxacin, rufloxacin, balofloxacin, levofloxacin, norfloxacin, ciprofloxacin, pazufloxacin, sparfloxacin, tosufloxacin, clinafloxacin, gemifloxacin, sitafloxacin, prulifloxacin and combinations thereof.

Non-limiting examples of anti-bacterial agents other than fluoroquinolones that may be used include vancomycin, teicoplanin, telavancin, decaplanin, ramoplanin, azitromycin, gentamicin, tobramycin, amikacin, cefuroxime, mitomycin, neomycin, neosporin, amoebicides (e.g., metronidazole, tinidazole, secnidazole, orornidazole, polyhexamethylene biguanide or chlorhexidine), polymyxin, clindamycin, bacitracin, chloramphenicol, erythromycin, natamycin, blephamide, sulfacetamide, sodium bicarbonate, povidone-iodine and combinations thereof.

In various embodiments, the concentration of the antiviral medicament(s) in the ophthalmological compositions of the present application may be between about 0.01 mg/mL and about 75.0 mg/mL, such as between about 1.0 mg/mL and about 50.0 mg/mL, for example, about 20.0 mg/mL. Non-limiting examples of the antiviral medicaments that may be used include idoxuridine, vidarabine and combinations thereof.

In various embodiments, the concentration of the antifungal medicament(s) in the ophthalmological compositions of the present application may be between about 0.01 mg/mL and about 75.0 mg/mL, such as between about 1.0 mg/mL and about 50.0 mg/mL, for example, about 20.0 mg/mL. Non-limiting examples of the antifungal medicaments that may be used are ketoconazole and fluconazole.

In various embodiments, the concentration of the immunosuppressant(s) in the ophthalmological compositions of the present application may be between about 0.01 mg/mL and about 50.0 mg/mL, such as between about 0.1 mg/mL and about 30.0 mg/mL, for example, about 20.0 mg/mL. Non-limiting examples of the immunosuppressants that may be used include tacrolimus, cyclosporine and combinations thereof.

As mentioned above, the pharmaceutical composition that is the subject matter of the instant application may further optionally include one or several pharmaceutically acceptable excipient(s). In some embodiments, an excipient that can be used may be a non-ionic polyoxyethylene-polyoxypropylene block copolymer having the following general structure:

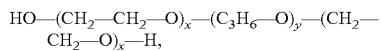

wherein x is an integer having the value of at least 8 and y is an integer having the value of at least 38.

If a non-ionic polyoxyethylene-polyoxypropylene block copolymer is used as an excipient, its contents in the overall composition may be between about 0.01 mass % and about 20.0 mass %, such as between about 1.0 mass % and about 15 mass %, for example, about 10.0 mass %.

One non-limiting example of a specific non-ionic polyoxyethylene-polyoxypropylene block copolymer that can be used as a solubilizing and stabilizing agent in the pharmaceutical compositions of the instant invention is the product known under the trade name Poloxamer 407® (poly(ethylene glycol)-block-poly(propylene glycol)-block-poly(ethylene glycol)) available from Sigma-Aldrich Corp. of St. Louis, Mo., with the molecular weight of the polyoxypropylene portion of about 4,000 Daltons, about a 70% polyoxyethylene content, the overall molecular weight of between about 9,840 Daltons and about 14,600 Daltons and having the following chemical structure:

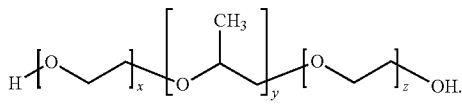

According to further embodiments, the excipient portion of the pharmaceutical formulation may contain other products, instead of, or in combination with, non-ionic polyoxyethylene-polyoxypropylene block copolymer(s). One non-limiting example of such additional excipient is poly(acrylic acid) in its various cross-linked or non-cross-linked versions, such as Carbomer 940® having a weight-average molecular weight of about 940 and available from Lubrizol Corp. of Wickliffe, Ohio. Another type of product that can be used in the excipient portion of the pharmaceutical formulation may be water-soluble methylcellulose and hydroxypropyl methylcellulose polymers, such as METHOCEL® family of products available from Dow Chemical Co. of Midland, Mich., for example, a hydroxypropyl methylcellulose product METHOCEL® E4M.

According to further embodiments, methods for fabricating the above-described pharmaceutical compositions are provided. A one-batch formulation method may be used, where the components of the pharmaceutical formulation can be combined in single container; the components may be added to the container simultaneously or consecutively. Alternatively, a two- or multiple-batch method(s) may be used if desired, where each component of the pharmaceutical formulation can be combined in a separate container followed by combining the contents of each container.

In one exemplary, non-limiting procedure, a quantity of a tumor necrosis factor inhibitor such as pentoxifylline may be placed into a mixing container followed by adding a quantity of sterile water and a polymeric gel (e.g., a Poloxamer 407®-based gel); the mixture is stirred until a clear stable solution is obtained, allowing the formulation to remain closed system thus preventing contamination and the loss of sterility.

The resulting product may then be transferred into single dose vials, capped, sealed, autoclaved and shaken until cool. Finally, a complete sterility and endotoxin may be performed on the product according to commonly used methods known to those having ordinary skill in the art. As mentioned above, in some embodiments, the pharmaceutical compositions can be used for topical administration such as compositions formulated and delivered to a patient as eye drops. The compositions may also contain some quantity of preservative(s) such as benzalkonium chloride, if desired.

It will be understood by those having ordinary skill in the art that the specific dose level and frequency of dosage for any particular patient may be varied and will depend upon a variety of factors including the activity of the specific compound employed, the metabolic stability and length of action of that compound, the age, body weight, general health, gender, diet, and the severity of the particular ophthalmological condition being treated.

It is additionally envisioned that in some embodiments pharmaceutical formulations disclosed herein may be used in combination with other products that are intended to improve tear production. Non-limiting examples of such other products include artificial tears of any kind, e.g., those containing hyaluronic acid, carboxymethyl cellulose, hydroxypropyl methylcellulose, polyvinyl alcohol, hydroxypropyl cellulose and derivatives thereof. Those having ordinary skill in the art and desiring to use the combinations of the presently described formulations with artificial tears may design the method of administering the combinations. For example, the presently described formulations may be pre-mixed with artificial tears and thus the present formulations may be administered simultaneously with artificial tears. Alternatively, consecutive administering without pre-mixing is also viable.

In additional embodiments, pharmaceutical kits are provided. The kit includes a sealed container approved for the storage of pharmaceutical compositions, the container containing one of the above-described pharmaceutical compositions and a device for topically administering the formulation (e.g., an eye dropper). An instruction for the use of the composition and the information about the composition are to be included in the kit.

The following examples are provided to further elucidate the advantages and features of the present invention, but are not intended to limit the scope of the invention. The examples are for the illustrative purposes only. USP pharmaceutical grade products were used in preparing the formulations described below.

Example 1

Preparing a Pharmaceutical Composition No. 1

A pharmaceutical composition was prepared as described below. The following components were used in the amounts and concentrations specified:
(a) about 20.0 g of aqueous solution of Poloxamer 407®, at a concentration of Poloxamer 407® of about 20.0 mass %;
(b) about 0.11 g of Carbomer 940® (a powder); and
(c) about 100.0 mL of sterile water for injection.

Poloxamer 407® and Carbomer 940® were thoroughly mixed with water, until fully dissolved, the pH was adjusted to about 5.5 using sodium hydroxide. The product was then refrigerated overnight, placed into a vial and autoclaved followed by adding the preservative benzalkonium chloride (at about 1:10,000 mass ratio) to form a stock Poloxamer/Carbomer gel to be used in further steps. Next, the following products were used in the amounts and concentrations specified:
(d) about 1.0 g of pentoxifylline, at a concentration of about 1.0%;
(e) about 90 mL of the Poloxamer/Carbomer gel obtained as described above; and
(f) about 9.0 mL of sterile water for injection.

Pentoxifylline was combined with the gel and water and the final product was transferred into dropper bottles (10 mL size), capped and sealed. The product has an estimated shelf life of about 90 days when kept refrigerated.

Example 2

Preparing a Pharmaceutical Composition No. 2

A pharmaceutical composition was prepared as described below. The following components were used in the amounts and concentrations specified:
(a) about 0.4 g of METHOCEL® E4M (a powder);
(b) about 0.2 g of Carbomer 940® (a powder); and
(c) about 100.0 mL of sterile water for injection.

The METHOCEL® E4M and Carbomer 940® powders were combined in a beaker, then water was added to allow hydrating overnight to form a solution, the pH was adjusted to about 5.0 using sodium hydroxide. The gel was autoclaved and cooled followed by adding preservative benzalkonium chloride (at about 1:10,000 mass ratio) to form a stock METHOCEL® E4M/Carbomer solution to be used in further steps. Next, the following components were used in the amounts and concentrations specified:
(d) about 1.0 g of pentoxifylline, at a concentration of about 1.0%;
(e) about 90 mL of the METHOCEL® E4M/Carbomer solution obtained as described above; and
(f) about 9.0 mL of sterile water for injection.

Pentoxifylline was combined with the gel and water and the final product was transferred into dropper bottles (10 mL size), capped and sealed. The product has an estimated shelf life of about 90 days when kept refrigerated.

Although the invention has been described with reference to the above examples, it will be understood that modifications and variations are encompassed within the spirit and scope of the invention. Accordingly, the invention is limited only by the following claims.

What is claimed is:

1. A pharmaceutical composition comprising:
(a) a therapeutically effective amount of at least one compound selected from the group consisting of pentoxifylline, lisofylline, am inophylline, enprofylline, isbufylline, and combinations thereof, or a pharmaceutically acceptable salt(s), solvate(s) or hydrate(s) thereof;
(b) a therapeutically effective amount of an immunosuppressant selected from the group consisting of cyclosporine, tacrolimus, and combinations thereof; and
(c) a pharmaceutically acceptable carrier or excipient comprising a non-ionic polyoxyethylene-polyoxypropylene block copolymer, at a concentration of between about 0.01 mass % and about 1.0 mass % of the entire formulation,
wherein the pharmaceutical composition is adapted for improving tear production in a mammalian subject suffering from an insufficient secretion thereof.

2. The pharmaceutical composition of claim 1, wherein the excipient further comprises a polymer selected from the group consisting of poly(acrylic acid), methylcellulose, hydroxypropyl methylcellulose, and combinations thereof.

3. The pharmaceutical composition of claim 1, further comprising an active agent selected from the group consisting of at least one anti-bacterial agent, at least one antiviral medicament, at least one antifungal medicament, at least one immunosuppressant, and combinations thereof.

4. The pharmaceutical composition of claim 3, wherein the anti-bacterial agent is selected from the group consisting of moxifloxacin, gatifloxacin, nalidixic acid, oxolinic acid, piromidic acid, pipemidic acid, rosoxacin, enoxacin, fleroxacin, lomefloxacin, nadifloxacin, ofloxacin, pefloxacin, rufloxacin, balofloxacin, levofloxacin, norfloxacin, ciprofloxacin, pazufloxacin, sparfloxacin, tosufloxacin, clinafloxacin, gemifloxacin, sitafloxacin, prulifloxacin, vancomycin, teicoplanin, televancin, decaplanin, ramoplanin, azitromycin, gentamicin, tobramycin, am ikacin, cefuroxime, mitomycin, neomycin, neosporin, amoebicides, polymyxin, clindamycin, bacitracin, chloramphenicol, erythromycin, natamycin, blephamide, sulfacetamide, sodium bicarbonate, povidone-iodine, and combinations thereof.

5. The pharmaceutical composition of claim 3, wherein the antiviral medicament is selected from the group consisting of idoxuridine, vidarabine, and combinations thereof.

6. The pharmaceutical composition of claim 3, wherein the antifungal medicament is selected from the group consisting of ketoconazole, fluconazole, and combinations thereof.

7. The pharmaceutical composition of claim 1, wherein the concentration of the compound in the composition is between about 0.03 millimoles and about 3 millimoles of the compound per 1 μL of the composition.

8. The pharmaceutical composition of claim 1, wherein the insufficient tear secretion is caused by a disease, syndrome or pathology selected from the group consisting of keratoconjunctivitis sicca, Stevens-Johnson syndrome, age-related dry eye, ocular cicatricial pemphigoid, neurotrophic ocular surface disease and blepharitis.

9. The pharmaceutical composition of claim 8, wherein the disease is keratoconjunctivitis sicca.

10. The pharmaceutical composition of claim 1, wherein the compound is pentoxifylline or a pharmaceutically acceptable salt thereof.

11. The pharmaceutical composition of claim 1 consisting essentially of a therapeutically effective amount of pentoxifylline or a pharmaceutically acceptable salt, solvate or hydrate thereof, and a pharmaceutically acceptable excipient or carrier suitable for eye drop administration.

12. The pharmaceutical composition of claim 1, wherein the composition is formulated in the form of eye drops.

13. A kit comprising:
    (a) the pharmaceutical composition of claim 1;
    (b) a device for topically administering the formulation;
    (c) a container for housing the pharmaceutical composition and the delivery device; and
    (d) instructions for use.

* * * * *